United States Patent [19]
Jung et al.

[11] Patent Number: 4,874,887
[45] Date of Patent: Oct. 17, 1989

[54] PROCESS FOR THE PREPARATION OF PYRETHROID TYPE ESTER COMPOUNDS

[75] Inventors: Sang H. Jung; Seung K. Kim, both of Chungcheongnam, Rep. of Korea

[73] Assignee: Lucky, Ltd., Seoul, Rep. of Korea

[21] Appl. No.: 259,267

[22] PCT Filed: Feb. 2, 1988

[86] PCT No.: PCT/KR88/00003
§ 371 Date: Oct. 7, 1988
§ 102(e) Date: Oct. 7, 1988

[87] PCT Pub. No.: WO88/06151
PCT Pub. Date: Aug. 25, 1988

[30] Foreign Application Priority Data
Feb. 13, 1987 [KR] Rep. of Korea ............... 87 1205
Feb. 13, 1987 [KR] Rep. of Korea ............... 87 1206

[51] Int. Cl.$^4$ .......................... C07C 121/75
[52] U.S. Cl. ...................... 560/124; 558/345; 558/351; 558/398; 558/40; 558/407; 560/55; 560/105
[58] Field of Search ............ 560/55, 105, 124; 558/351, 345, 398, 406, 407

[56] References Cited
U.S. PATENT DOCUMENTS

| | | | |
|---|---|---|---|
| 4,110,360 | 8/1978 | Sheldon | 558/345 |
| 4,110,361 | 8/1978 | Sheldon | 558/345 |
| 4,110,362 | 8/1978 | Sheldon | 558/345 |
| 4,110,363 | 8/1978 | Sheldon | 558/345 |
| 4,123,451 | 10/1978 | Sheldon | 558/345 |
| 4,175,093 | 11/1979 | Reinink | 558/345 |
| 4,175,094 | 11/1979 | Reinink | 558/345 |
| 4,244,168 | 1/1984 | Collin | 558/345 |
| 4,254,050 | 3/1981 | Baum | 558/345 |
| 4,254,051 | 3/1981 | Baum | 558/345 |
| 4,254,052 | 3/1981 | Baum | 558/345 |
| 4,280,965 | 7/1981 | Hartman | 558/345 |
| 4,299,776 | 11/1981 | Hatch | 558/345 |
| 4,350,640 | 9/1982 | Fuchs | 558/345 |
| 4,382,894 | 5/1983 | Tissington | 558/345 |
| 4,409,150 | 10/1983 | Wood | 558/407 |

FOREIGN PATENT DOCUMENTS
288427 10/1988 European Pat. Off. ............ 558/351

Primary Examiner—Michael L. Shippen
Attorney, Agent, or Firm—Needle & Rosenberg

[57] ABSTRACT

The present invention relates to a novel process for the preparation of insecticidally active esters of the general formula (I)

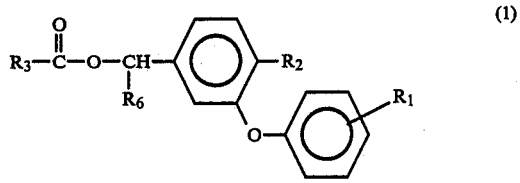

wherein $R_1$ and $R_2$ are the same or diferent from each other and represent a hydrogen or a halogen atom; $R_3$ represents

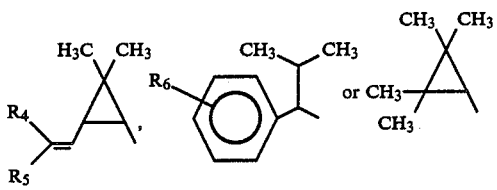

(wherein $R_4$ and $R_5$ represent a chlorine or bromine atom or a methyl group when $R_4$ is identical to $R_5$, but $R_4$ represents a chlorine or bromine atom or a methyl group and $R_5$ represents a trifluoromethyl group when $R_4$ is different from $R_5$, and $R_6$ represents a halogen atom or a difluoromethoxy group); and $R_8$ represents a hydrogen or a cyano group.

The characteristic of the present invention is a one-step procedure comprising directly condensing an organic acid, an aldehyde (and a water-soluble cyanide) in the presence of a phase transfer catalyst and a water-soluble inorganic base by the use of a sulphonyl compound as a condensing reagent.

20 Claims, No Drawings

PROCESS FOR THE PREPARATION OF PYRETHROID TYPE ESTER COMPOUNDS

BACKGROUND OF THE INVENTION

The present invention relates to a novel process for the preparation of insecticidally active esters of the general formula(I):

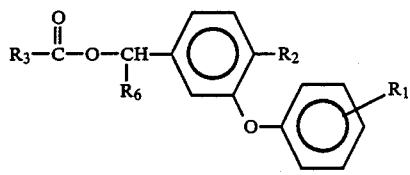

wherein $R_1$ and $R_2$ are the same or different from each other and represent a hydrogen or a halogen atom; $R_3$ represents

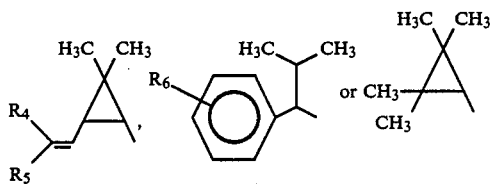

(wherein $R_4$ and $R_5$ represent a chlorine or bromine atom or a methyl group when $R_4$ is identical to $R_5$, but $R_4$ represents a chlorine or bromine atom or a methyl group and $R_5$ represents a trifluoromethyl group when $R_4$ is different from $R_5$, and $R_6$ represents a halogen atom or a difluoromethoxy group); and $R_8$ represents a hydrogen or a cyano group.

It is known, according to the following methods, that the publicly known process for the preparation of the compound of formula(I) wherein $R_8$ is a cyano group, which is used for pesticides and acaricides.

(A) U.K. Patent Specification No. 1,540,632 discloses a process for the preparation of an ester of the general formula (3) wherein A is an optionally-substituted alkyl or cycloalkyl group and B is a phenoxy, phenylthio or benzyl, which comprises reacting a benzaldehyde of the formula (2) with an acyl halide of the formula (1) (wherein $X_1$ is a bromine or chlorine atom) in the presence of water, a water-soluble cyanide, a substantially water-immiscible aprotic solvent and a phase transfer catalyst.

The reaction formula of the above process is as follows;

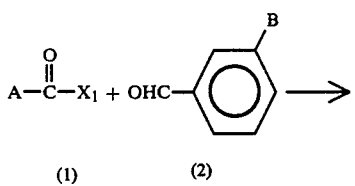

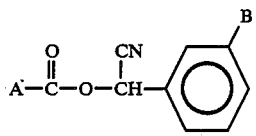

The acyl halide of formula (1) should be prepared by reacting a halogenation reagent such as thionyl chloride with an organic acid. However, because the halogenation reagent is sensitive to moisture, it is unstable in an atmosphere with a high moisture content and the reactor should be dried before each reaction. Also corrosion of the reactor occurs easily since hydrogen chloride and sulfurous acid gases are produced as byproducts. Thus, when they are not appropriately treated, they cause a pollution problem. Because the reactivity of the acyl halide of formula (1), an intermediate, is great and it decomposes readily in the presence of water and heat, purification is difficult and a specific apparatus must be used.

(B) German Patent No. 2,651,341 discloses a process for the preparation of an ester of the general formula (3) wherein A and B are the same as the above-mentioned, which comprises neutralizing an acid of the formula (4) with a water-soluble base and reacting the product with a halide of the formula (5) (wherein $X_2$ is a halogen atom) in the presence of water, a substantially water-immiscible aprotic solvent and a phase transfer catalyst.

The reaction formula of the above process is as follows;

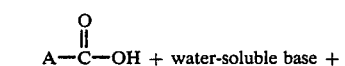

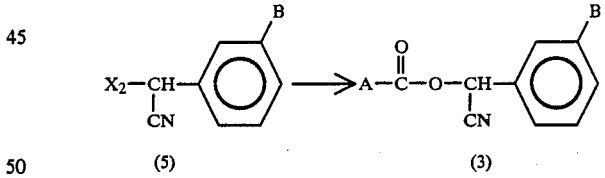

The halide of the formula (5) is a compound derived from an alcohol precursor whose industrial preparation is difficult.

Because the halogenation reagent must be used as mentioned in (A) so as that the alcohol is converted to the halide, there are the same problems as in (A).

(C) U.S. Pat. No. 4,409,150 discloses a method for preparing a pyrethroid insecticide of the general formula (9) wherein $A_1$ is a cycloalkyl and $B_1$ and $B_2$ represent hydrogen or halogen atoms, in which an acid of formula (7) is neutralized with a water-soluble base and then reacted in the presence of a phase transfer catalyst with a solution in a substantially water-immiscible organic solvent of an alpha-cyanobenzyl arylsulphonate of formula (8) wherein $B_3$ represents an optionally substituted aryl group.

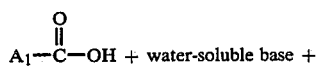

(7)

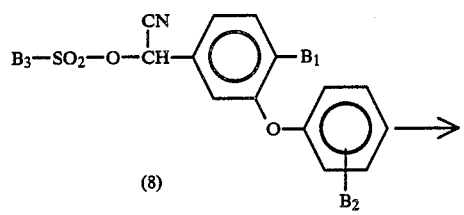

The alpha-cyanobenzyl arylsulphonate of formula (8) is prepared by reacting a benzaldehyde and a water-soluble cyanide. After separating the sulphonates of formula (8), unstable intermediates, they are reacted with an acid of formula (7) in order to prepare an ester of formula (9) and then the complexity of the procedure itself becomes a difficult problem.

Also, pursuant to the following methods, the process for the production of the compound of formula (I) wherein $R_8$ is a hydrogen is known.

(D) German Patent No. 2,326,077 discloses a process for the preparation of an ester of the general formula (12) comprising condensing an acyl halide of formula (10) with an alcohol of formula (11) in the presence of an organic base as represented in the following reaction formula.

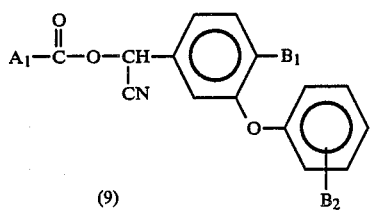

The acyl halide of formula (10) must be prepared by reacting a halogenation reagent such as thionyl chloride with an organic acid. But as mentioned in the explanation of (A), there are some problems and drawbacks.

(E) German Patent No. 2,437,882 discloses a process for the preparation of an ester of the general formula (12), which comprises reacting a metal salt of an organic acid of formula (13) wherein M is an alkali metal, with a quaternary ammonium, as shown in the following reaction formula.

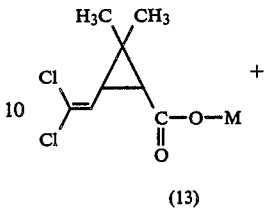

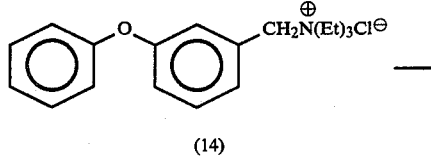

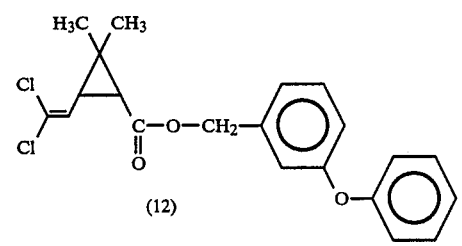

(F) German Patent No. 2,544,150 discloses a process for the preparation of an ester of the general formula (12) comprising reacting a lower alkyl ester of formula (15) with an alcohol of formula (11) in the presence of a titanium catalyst to trans-esterify, as represented in the following reaction formula.

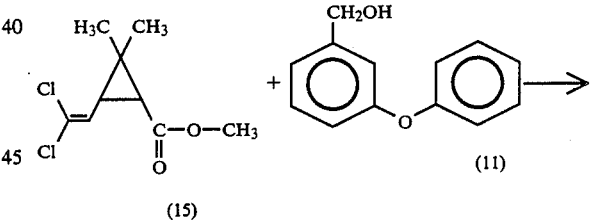

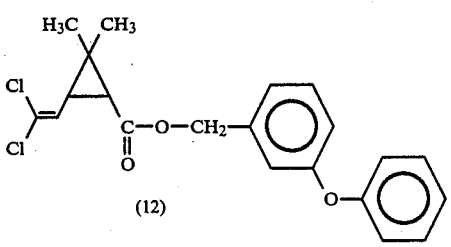

In the above-mentioned prior arts (E) and (F), because the organic acid or one of the alcohol reactants is prepared by condensation after it has been made into a functional derivative and then activated, there are some inconvenient steps in the procedure.

SUMMARY OF THE INVENTION

The object of the present invention is to provide a synthetic route which facilitates the production of the compound of formula (I) in good yield and high purity by eliminating the above mentioned problems of the prior arts.

Firstly, the process for the preparation of the compound of formula (I-1) comprises reacting an organic acid of formula (II), an aldehyde of formula (III) and a water-soluble cyanide with a sulphonyl compound of formula (IV) in the presence of a two-phase solvent system comprising water and a substantially water-immiscible aprotic solvent and a phase transfer catalyst, and then reacting the reaction mixture with a water-soluble inorganic base, wherein $R_1$, $R_2$ and $R_3$ are as defined above, $R_7$ represents an aryl, alkyl or an optionally-substituted aryl and X is a halogen, azide, cyanide, imidazole, triazole, nitrotriazole, or tetrazole.

The reaction formula of the above procedure may be shown as follows;

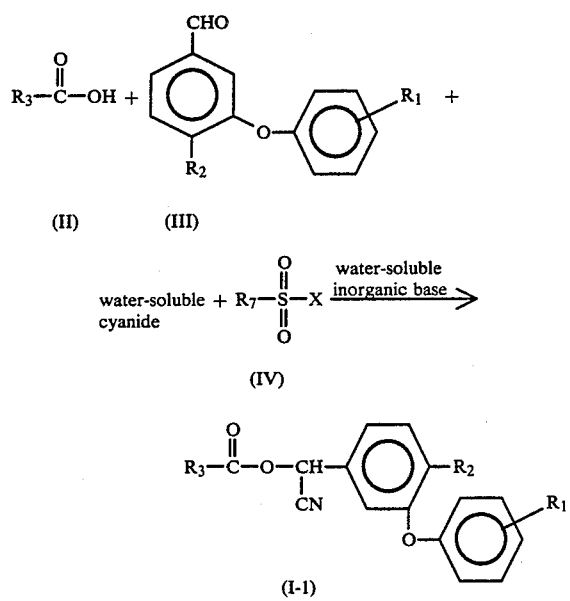

Secondly, the process for the preparation of the compound of formula (I-2) comprises reacting an organic acid of formula (II), an alcohol of formula (III') and a water-soluble inorganic base with a sulphonyl compound of formula (IV) in the presence of a two-phase solvent system comprising water and a substantially water-immiscible aprotic solvent and a phase transfer catalyst, wherein $R_1, R_2, R_3, R_7$ and X are as defined above. This process is represented by the following reaction formula.

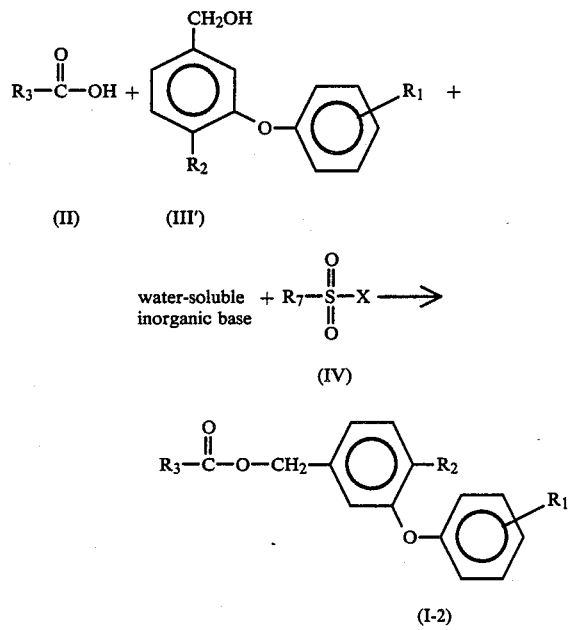

The compound of formula (I-1) is the compound of formula (I) wherein $R_8$ is a cyano group and the compound of formula (I-2) is the compound of formula (I) wherein $R_8$ is a hydrogen.

DETAILED DESCRIPTION OF A PREFERRED EMBODIMENT

One of the characteristics of the present invention is that it is not a multi-step procedure which comprises preparing the functional derivatives of an organic acid or an alcohol and then condensing, but is a one-step procedure comprising directly condensing an organic acid, an aldehyde and a water-soluble cyanide in the presence of a phase transfer catalyst and a water-soluble inorganic base by the use of a sulphonyl compound of formula (IV) as a condensing reagent, in preparing an alpha-cyano ester compound of formula (I-1).

The process for the preparation of the compound of formula (I-1) may be represented by the following diagram I.

DIAGRAM I

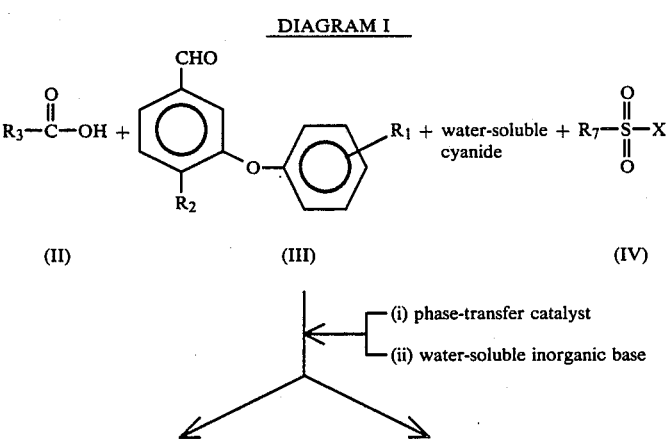

DIAGRAM I -continued

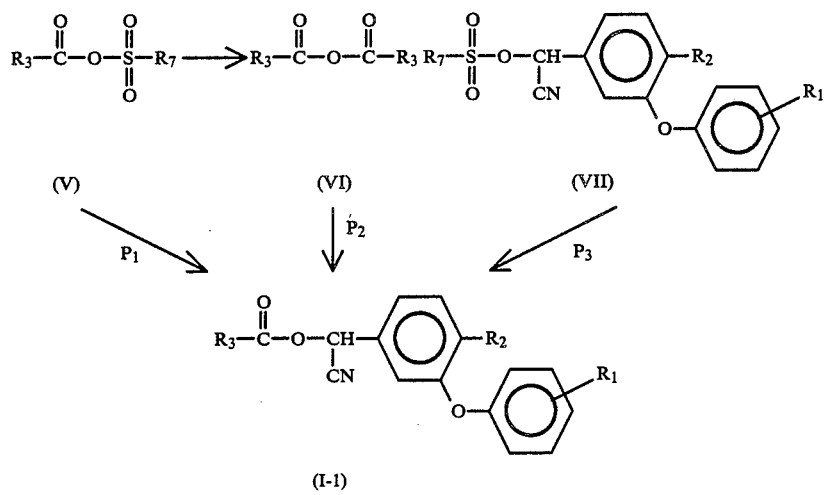

(I-1)

The substituents $R_1$, $R_2$, $R_3$, $R_7$ and X in diagram I are as defined above and $P_1$, $P_2$ and $P_3$ represent individual reaction pathways.

From the above pathways, the present inventors have found that the compound of formula (I-1) is prepared via the three intermediates represented by the general formulas (V), (VI) and (VII) and the primary pathway is the $P_1$ reaction pathway which comprises an intermediate of formula (V) by confirming that the percentage of intermediates and thus their respective respective pathways, $P_1$, $P_2$ and $P_3$ is 60:30:10. Namely, the present invention which is different from the many previously publicly known synthetic methods, concerns a process for the production of formula (I-1) which comprises mixed intermediates consisting of the publicly known intermediates of formula (VI) and (VII) to some extent and a new intermediate of formula (V) to a great extent.

According to the present invention, the reaction is carried out in a short time under mild reaction conditions, and does not form pollution causing byproducts. Also there is merit in the direct, one-step process, such that an ester of formula (I-1) may be produced in greater yield with high purity without separating the functional derivatives of an organic acid or an alcohol.

Meanwhile, according to the prior art (A) of U.K. Patent Specification No. 1,540,632, when cis-alpha-cyano-3-phenoxybenzyl-3-(2,2-dichlorovinyl)-2,2-dimethylcyclopropanecarboxylate is prepared from a pure cis-3-(2,2-dichlorovinyl)-2,2-dimethylcyclopropane carboxylic acid, its purity is 95% and the ratio of cis- and trans-isomers is 95:5 (w/w). Namely, 5% of the cis configuration is isomerized to the trans configuration. But according to the present invention, an ester of pure cis configuration can be obtained in good yield, without isomerization.

The phase transfer catalyst of the present invention may be any reagent which does not influence the reaction, particularly a quaternary ammonium or phosphonium compound. Generally economic considerations make it preferable to use quaternary ammonium compounds and examples include tetra-n-butylammonium bromide, tetra-n-butylammonium chloride, cetyltrimethylammonium bromide, tetra-n-butylammonium iodide, methyltri($C_{8-10}$ alkyl)ammonium chloride and also methyltri-2-methylphenylammonium chloride.

Alternatively, the macrocyclic polyesters known as "crown ethers" may be utilized as phase transfer catalysts. These compounds, together with their preparation, are described in the literature, for example in Tetrahedron Letters No. 18 (1977) pp. 1793–1796, and are commonly designated by reference to the total number of atoms forming the macrocyclic ring together with the number of oxygen atoms in that ring. Thus the macrocyclic polyester whose formal chemical name is 1,4,7,10,13,16-hexaoxacyclooctadecane is designated as "18-crown-6". Other examples of suitable macrocyclic polyethers are dicyclohexyl-18-crown-6 and dibenzo-18-crown-6,2,1,1-kryptate.

Other types of compounds which may be used as phase transfer catalysts include amine and quaternary ammonium ion exchange resins, for example, 2,4-dimethyl-2,4-diazapentane; 2,5-dimethyl-2,5-diazahexane; N,N,N',N'-tetramethyl-1,2-diamino cyclohexane; 1,4-dimethyl-1,4-diazacyclohexane; 2,7-dimethyl-2,7-diaza-4-octane; 1,4-diazobicyclo[2,2,2] octane; 2,6-dimethyl-2,6-diazaheptane, 2,9-dimethyl-2,9-diazadecane, and 2,5,8,11-tetramethyl-2,5,8,11-tetraazadodecane.

The molar ratio of the amount of phase transfer catalyst to the amount of benzaldehyde of the general formula(III) may vary from 1:5 to 0.1:100, but is preferably from 1:10 to 1:20 in view of the reaction time and economics.

The organic solvent used in the present invention is a substantially water-immiscible aprotic solvent, for example, benzene, toluene, petroleum ethers, xylene, trimethyl benzene, tetrachloromethane, kerosene, dichloroethane or dichloromethane. Also the organic solvent may be one which does not influence the reaction materials. The temperature at which the process is conducted ranges from 0° C. to 100° C. and is preferably in the range of 10° C. to 80° C.

The molar ratio of the amount of water-soluble cyanide to the amount of aldehyde of formula(III) is suitably from 1.5:1 to 1.0:1.0 and preferably from 1.3:1 to 1.02:1.00. The term "water-soluble cyanide" means a water-soluble salt of hydrogen cyanide. Of the water-soluble cyanides, alkali metal cyanides and alkaline earth metal cyanides are preferred, and sodium cyanide is especially preferred.

The molar ratio of the amount of organic acid of formula(II) to the amount of aldehyde of formula(III) is 1:1 or slightly in excess thereof and this molar ratio is preferably in the range of 1.1:1.0 to 1.3:1.0.

Examples of suitable sulphonyl compounds of formula (IV) include p-toluene sulphonyl chloride, methane sulphonyl chloride, benzene sulphonyl chloride, p-toluene sulphonyl bromide, p-toluene sulphonyl azide and p-toluene sulphonyl cyanide; p-toluene sulphonyl chloride is particularly preferred.

The molar ratio of the amount of sulphonyl compound of formula (IV) to the amount of aldehyde of formula(III) is suitably 1:1 and preferably 1.05:1 to 1.3:1 in order to reduce the reaction time.

A useful reaction time is at least 1 hour and is preferably 3 to 6 hours.

Water-soluble inorganic bases according to the present invention are carbonates, bicarbonates and hydroxides of alkali metals or alkaline earth metals and particularly potassium carbonate or sodium carbonate in view of the reaction time and product yield.

The molar ratio of the amount of water-soluble inorganic base to the amount of aldehyde is 1:1 or slightly in excess thereof and preferably in the range from 2:1 to 3:1.

The other characteristic of the present invention is a one-step procedure comprising directly condensing an organic acid and an alcohol in the presence of a phase transfer catalyst and a water-soluble inorganic base by the use of a sulphonyl compound of formula (IV) as a condensing reagent, in preparing a benzyl ester compound of formula(I-2).

The process for the preparation of the compound of formula(I-2) may be represented by the following diagram II.

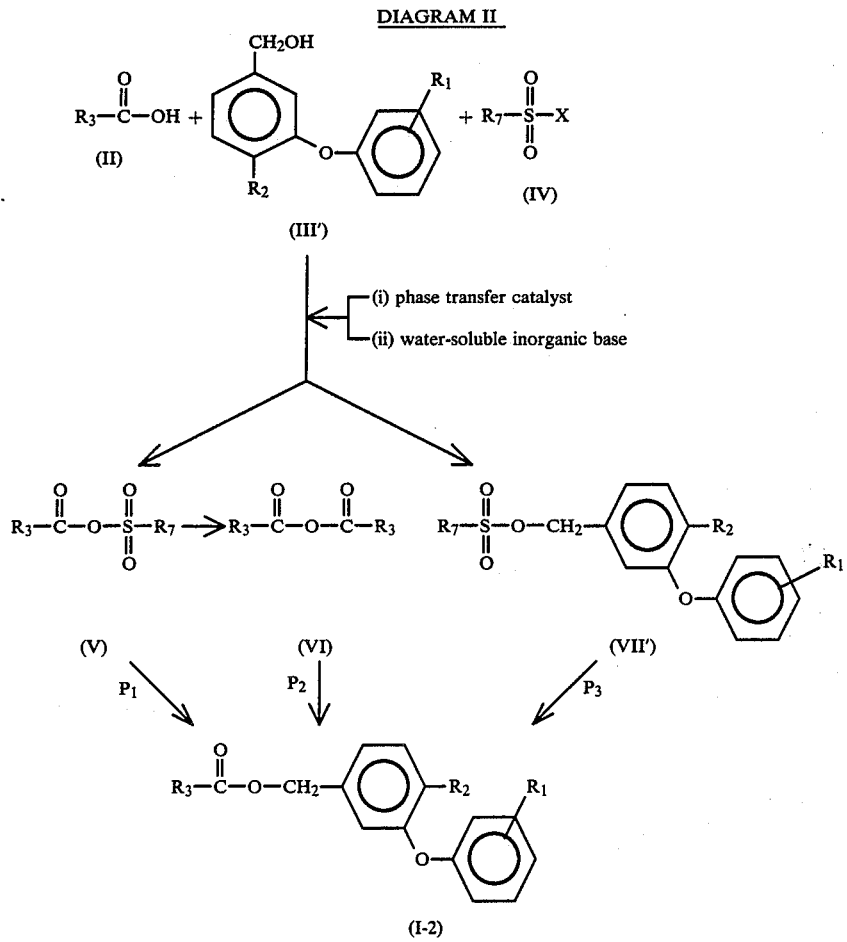

The substituents $R_1$, $R_2$, $R_3$, $R_7$ and X in diagram II are as defined above and $P_1$, $P_2$ and $P_3$ represent individual reaction pathways.

From the above pathways according to the present invention, the inventors have found that the object ester compound of formula(I-2) is obtained via the three intermediates represented as general formulas (V), (VI) and (VII') using $P_1$, $P_2$ and $P_3$ pathways and the main pathway is the $P_1$ reaction pathway which comprises an intermediate of formula(V). The percentage of intermediates and thus their respective reaction pathways, $P_1$, $P_2$ and $P_3$, has been confirmed and is 80:15:5.

Namely, the present invention which is different from previously known synthetic methods, concerns a process for the production of formula(I-2) which comprises mixed intermediates consisting of the publicly known intermediates of formula(VI) to some extent and the new intermediates of formula(V) and (VII') to a great extent.

According to the present invention, the reaction is carried out in a short time under mild reaction conditions, and does not form byproducts which cause pollution. Also there is merit to a direct and one-step process in which a benzyl ester of formula(I-2) may be produced in greater yield with high purity without separating the functional derivatives of an organic acid or an alcohol.

The phase transfer catalyst is as exemplified in the above process for the preparation of an ester of formula(I-1) and the molar ratio of the amount of phase transfer catalyst to the amount of alcohol of formula(III') may be from 1:100 to 1:5, preferably from 1:20 to 3:20 in view of the reaction time and from an economic point of view.

The molar ratio of the amount of an organic acid of formula (II) to the amount of alcohol of formula(III') is 1:1 or slightly in excess thereof and preferably in the range of 1.1:1.0 to 1.2:1.0 from the point of reaction time and economics.

Also examples of suitable sulphonyl compounds of formula(IV) are the same as those of the process for the preparation of an ester of formula(I-1) and p-toluenesulphonyl chloride is particularly preferred. The molar ratio of the amount of sulphonyl compounds of formula(IV) to the amount of alcohol of formula(III') is suitably 1:1 and preferably 1.1:1 to 1.4:1 in order to reduce the reaction time.

Water-soluble inorganic bases according to the present invention are as exemplified in the above process for the preparation of an ester of formula(I-1) and the molar ratio of the amount of water-soluble inorganic base to the amount of alcohol of formula (III') may be 2:1 or slightly in excess thereof and preferably from 3:1 to 4.5:1.

The organic solvents used in the present invention, the reaction temperature and useful reaction times are as mentioned above.

The invention is illustrated by the following examples, without them limiting its range. The purity of the products of the examples was analyzed using gas-chromatography and the yield is based upon the respective starting material, namely, an aldehyde or alcohol.

EXAMPLE 1

Preparation of alpha-cyano-3-phenoxybenzyl cis, trans-3-(2,2-dichlorovinyl)-2,2-dimethylcyclopropanecarboxylate A 3 l round-bottom flask equipped with a thermometer and a stirrer was charged with 198.22 g (1 mol) of 3-phenoxybenzaldehyde, 25.88 g(1.2 mol) of cis, trans-3-(2,2-dichlorovinyl)-3, 3-dimethylcyclopropanecarboxylic acid, 58.31 g(1.2 mol) of sodium cyanide, 6.17 g (0.055 mol) of 1,4-diazabicyclo [2,2,2] octane, 113.40 g (6.3 mol) of water and 1,000 g of toluene. The mixture thus formed was stirred at 20°–30° C. for 30 minutes.

247.85 g (1.2 mol) of p-toluene sulphonyl chloride was added to the above mixture which was stirred for an additional 20 minutes at 20°–30° C. Then 233.18 g(2.2 mol) of anhydrous sodium carbonate was added to it and maintained at the same temperature as above for 1 hour.

After stirring for another hour at ambient temperature, 19.07 g(0.1 mol) of p-toluene sulphonyl chloride was further added and the mixture further reacted for 1 hour. The mixture thus formed was heated to 70° C. and stirred for 1 hour to complete the reaction.

After the reaction was completed, the reaction mixture was cooled to ambient temperature and 1,200 g of 5% sodium hydroxide was added and stirred.

The aqueous phase was extracted with 200 g of toluene and the organic phase was separated and washed with 500 g of water.

After further phase-separation, the organic phase thus formed was dried with anhydrous magnesium sulfate. The precipitate was filtered and the solvent was evaporated from the filtrate under reduced pressure to obtain alpha-cyano-3-phenoxybenzyl cis, trans-3-(2,2-dichlorovinyl)-2,2-dimethylcyclopropane carboxylate as a clear yellow liquid (399.36 g, 96.0%).

EXAMPLES 2 to 7

Preparation of alpha-cyano-3-phenoxybenzyl cis, trans-3-(2,2-dichlorovinyl)-2,2-dimethylcyclopropanecarboxylate A 50 ml round-bottomed flask equipped with a magnetic stirrer and a thermometer was charged with 792.9 mg(4 mmol) of 3-phenoxybenzaldehyde, 1,003.5 mg (4.8 mmol) of cis, trans-3-(2,2-dichlorovinyl)-2,2-dimethylcyclopropanecarboxylic acid, 235.3 mg (4.8 mmol) of sodium cyanide, 24.7 mg (0.22 mmol) of 1,4-diazabicyclo [2,2,2] octane, 0.45 g (25.2 mmol) of water and 20 ml of toluene. The mixture thus formed was stirred at 20°–30° C. for 30 minutes.

A sulphonyl compound as listed in Table I was added to the mixture and stirred for 10 minutes.

Then 932.7 mg (8.8 mmol) of anhydrous sodium carbonate was added to the mixture and the same temperature as above was maintained for 1 hour.

After the mixture thus formed was stirred at ambient temperature for an additional hour, the sulphonyl compound as listed in Table I was further added and reacted until the aldehyde was exhausted.

The mixture was heated at 70° C. for 1 hour to complete the reaction.

The reaction mixture was then treated as in Example 1 to yield alpha-cyano-3-phenoxybenzyl cis, trans-3-(2,2-dichlorovinyl)-2,2-dimethylcyclopropanecarboxylate.

The yields obtained are given in Table I.

TABLE I

| Example No. | Sulphonyl compound Name | Amount (mmol) 1st | Amount (mmol) 2nd | Reaction time (hrs) | Ester Yield (%) |
| --- | --- | --- | --- | --- | --- |
| 2 | p-toluene sulphonyl chloride | 4.4 | 0.2 | 4.5 | 95.9 |
| 3 | p-toluene sulphonyl bromide | 4.8 | 0.8 | 5.0 | 94.0 |
| 4 | methane sulphonyl chloride | 4.4 | 0.8 | 8.0 | 95.2 |
| 5 | benzene sulphonyl chloride | 4.4 | 0.4 | 7.0 | 95.8 |
| 6 | p-toluene sulphonyl cyanide | 4.3 | 0.4 | 6.0 | 92.0 |
| 7 | p-toluene sulphonyl azide | 4.4 | 0.4 | 5.0 | 95.5 |

The ratio of cis- to trans-ester obtained was 45:55.

EXAMPLES 8 to 12

Preparation of alpha-cyano-3-phenoxybenzyl cis, trans-3-(2,2-dichlorovinyl)-2,2-dimethylcyclopropanecarboxylate Following the procedure of Example 2, but using different water soluble inorganic bases as listed in Table II, alpha-cyano-3-phenoxybenzyl cis, trans-3-(2,2-dichlorovinyl)-2,2-dimethylcyclopropanecarboxylate was prepared. The yields obtained are as indicated in Table II.

TABLE II

| Example No. | Water-soluble inorganic base | Amount (mmol) | Reaction time (hrs) | Ester Yield (%) |
|---|---|---|---|---|
| 8 | Anhydrous potassium carbonate | 8 | 4 | 93 |
| 9 | Sodium bicarbonate | 20 | 35 | 85 |
| 10 | Sodium hydroxide | 6 | 4 | 75 |
| 11 | Calcium carbonate | 20 | 40 | 80 |
| 12 | Lithium carbonate | 24 | 48 | 85 |

The ratio of cis- to trans-ester obtained was 45:55.

EXAMPLES 13 to 15

Preparation of alpha-cyano-3-phenoxybenzyl cis, trans-3-(2,2-dichlorovinyl)-2,2-dimethylcyclopropanecarboxylate Following the procedure of Example 2, but using the phase transfer catalysts as indicated in Table III, alpha-cyano-3-phenoxybenzyl cis, trans-3-(2,2-dichlorovinyl)-2,2-dimethylcyclopropanecarboxylate was prepared. The yields obtained are given in Table III.

TABLE III

| Example No. | Phase transfer catalyst | Amount (mmol) | Reaction time (hrs) | Ester (%) Yield |
|---|---|---|---|---|
| 13 | Tetrabutyl ammonium bromide | 0.22 | 6 | 92 |
| 14 | 18-crown-6 | 0.22 | 10 | 94 |
| 15 | Tetrabutylphosphonium bromide | 0.22 | 6 | 91 |

The ratio of cis- to trans-ester obtained was 65:55.

EXAMPLE 16

Preparation of alpha-cyano-3-phenoxybenzyl, (1R cis)-2,2-dimethyl-3-(2,2-dibromovinyl)cyclopropanecarboxylate Following the procedure of Example 2, but using (1R cis)-2,2-dimethyl-3-(2,2-dibromovinyl)cyclopropane carboxylic acid as an organic acid, alpha-cyano-3-phenoxybenzyl, (1R cis) 2,2-dimethyl-3-(2,2-dibromovinyl)cyclopropanecarboxylate was obtained as a yellow liquid in 95% yield.

EXAMPLE 17

Preparation of alpha-cyano-3-phenoxybenzyl cis-3-(2-chloro-3,3,3-trifluoroprop-1-ene-1-yl)-2,2-dimethylcyclopropanecarboxylate Following the procedure of Example 2, but using cis-3-(2-chloro-3,3,3-trifluoroprop-1-ene-1-yl)-2,2-dimethylcyclopropane carboxylic acid as an organic acid, alpha-cyano-3-phenoxybenzyl cis-3-(2-chloro-3,3,3-trifluoroprop-1-ene-1-yl)-2,2-dimethylcyclopropane carboxylate was obtained as a yellow liquid in 97% yield.

EXAMPLE 18

Preparation of (R,S)-cyano-3-phenoxybenzyl cis-2,2-dimethyl-3-(2,2-dichlorovinyl)cyclopropanecarboxylate Following the procedure of Example 2, but using cis-2,2-dimethyl-3-(2,2-dichlorovinyl)cyclopropanecarboxylate as an organic acid, (R,S)-cyano-3-phenoxybenzyl cis-2,2-dimethyl-3-(2,2-dichlorovinyl)cyclopropanecarboxylate was obtained in 96% yield.

EXAMPLE 19

Preparation of alpha-cyano-4-fluoro-3-phenoxybenzyl, 3-(2,2-dichlorovinyl)-2,2-dimethylcyclopropane carboxylate Following the procedure of Example 2, but using 4-fluoro-3-phenoxybenzaldehyde as an aldehyde, alpha-cyano-4-fluoro-3-phenoxybenzyl, 3-(2,2-dichlorovinyl)-2,2-dimethylcyclopropane carboxylate was obtained in 95% yield.

EXAMPLES 20 to 22

Following the procedure of Example 2, but using 2-(4-chlorophenyl)-3-methyl butyric acid in Example 20, (S)-2-(4-difluoromethoxyphenyl)-3-methyl butyric acid in Example 21 and 2,2,3,3-tetramethyl cyclopropane carboxylic acid in Example 22, the results as indicated in Table IV were obtained.

TABLE IV

| Example No. | Product | Ester Yield (%) |
|---|---|---|
| 20 | [structure: 4-chlorophenyl isopropyl CH-C(=O)-O-CH(CN)-(3-phenoxyphenyl)] | 92 |
| 21 | [structure: 4-(F$_2$CHO)phenyl isopropyl CH-C(=O)-O-CH(CN)-(3-phenoxyphenyl), with H shown on stereocenter] | 91 |
| 22 | [structure: 2,2,3,3-tetramethylcyclopropane-C(=O)-O-CH(CN)-(3-phenoxyphenyl)] | 90 |

EXAMPLES 23 to 26

Following the procedure of Example 2, but using 4-fluoro-3-(4-chlorophenoxy)benzaldehyde and 3-(2,2-dichlorovinyl)-2,2-dimethyl cyclopropanecarboxylic acid in Example 23, 4-fluoro-3-(4-chlorophenoxy)benzaldehyde and cis-3-(2-chloro-3,3,3-trifluoroprop-1-ene-1-yl)-2,2-dimethylcyclopropanecarboxylic acid in Example 24, 3-(4-chlorophenoxy)benzaldehyde and 3-(2,2-dichlorovinyl)-2,2-dimethylcyclopropanecarboxylic acid in Example 25, and 3-(4-chlorophenoxy)benzaldehyde and cis-3-(2-chloro-3,3,3-trifluoroprop-1-ene-1-yl)-2,2-dimethylcyclopropane carboxylic acid in Example 26 as the aldehyde and the organic acid, respectively, the results as indicated in Table V were obtained.

droxide solution was injected into the reactor and the mixture was stirred.

The aqueous phase was extracted with 200 g of toluene and the organic phase was separated and washed with 500 g of water.

The organic phase thus formed was dried with anhydrous magnesium sulfate. The precipitate was filtered and the solvent was evaporated from the filtrate under reduced pressure to obtain 3-phenoxybenzyl cis, trans-3-(2,2-dichlorovinyl)-2,2-dimethylcyclopropane carboxylate as a clear yellow liquid(379.5 g). The ratio of cis- to trans-ester obtained was 45:55.

EXAMPLES 28–32

Preparation of 3-phenoxybenzyl cis, trans-3-(2,2-dichlorovinyl)-2,2-dimethylcyclopropane

TABLE V

| Example No. | Product | Ester Yield (%) |
|---|---|---|
| 23 | [structure] | 96 |
| 24 | [structure] | 95 |
| 25 | [structure] | 96 |
| 26 | [structure] | 97 |

EXAMPLE 27

Preparation of 3-phenoxybenzyl cis, trans-3-(2,2-dichlorovinyl)-2,2-dimethylcyclopropanecarboxylate A 3 l round-bottomed flask equipped with a stirrer and a thermometer was charged with 200.24 g (1 mol) of 3-phenoxybenzylalcohol, 229.98(1.1 mol) of cis, trans-3-(2,2-dichlorovinyl)-2,2-dimethyl cyclopropane carboxylic acid, 11.22 g(0.1 mol) of 1,4-diazabicyclo [2,2,2] octane, 113.40 g (6.3 mol) of water and 1,160 g of toluene. The mixture thus formed was stirred at 20°–30° C. for 30 minutes.

After stirring for an additional two hours at 20°–30° C., the mixture was heated to 70° C. and stirred for 30 minutes.

The mixture was cooled to ambient temperature after the reaction was completed. 1,600 g of 5% sodium hycarboxylate A 50 ml round-bottomed flask equipped with a magnetic stirrer and a thermometer was charged with 600.7 mg (3 mmol) of 3-phenoxybenzyl alcohol, 689.9 mg(3.3 mmol) of cis, trans-3-(2,2-dichlorovinyl)-2,2-dimethylcyclopropane carboxylic acid, 33.7 mg (0.3 mmol) of 1,4-diazabicyclo [2,2,2] octane, 0.34 mg (18.9 mmol) of water and 15 g of toluene. The mixture thus formed was stirred at 20° C. and 1,658.5 mg (12 mmol) of anhydrous potassium carbonate was added.

After stirring the mixture at 25°–30° C. for 1 hour, a sulphonyl compound as indicated in Table VI was added to the mixture and stirred for an additional two hours. The mixture was heated to 70° C. and stirred for 30 minutes to complete the reaction.

The reaction mixture was then treated as in Example 27 to yield 3-phenoxybenzyl cis, trans-3-(2,2- dichlorovinyl)-2,2-dimethylcyclopropanecarboxylate as a clear yellow liquid.

The yields obtained are given in Table VI.

The ratio of cis- to trans-ester obtained was 45:55.

TABLE VI

| Example No. | Sulphonyl compound | | Ester Yield (%) |
|---|---|---|---|
| | Name | Amount (mmol) | |
| 28 | p-toluene sulphonyl chloride | 3.6 | 97 |
| 29 | p-toluene sulphonyl bromide | 3.6 | 97 |
| 30 | methane sulphonyl chloride | 3.9 | 96 |
| 31 | benzene sulphonyl chloride | 3.6 | 97 |
| 32 | p-toluene sulphonyl cyanide | 3.9 | 96 |
| 33 | p-toluene sulphonyl azide | 3.3 | 95 |

EXAMPLES 34 to 38

Preparation of 3-phenoxybenzyl cis, trans-3-(2,2-dichlorovinyl)-2,2-dimethylcyclopropanecarboxylate Following the procedure of Example 28, but using the water-soluble inorganic base as indicated in Table VII, 3-phenoxybenzyl cis, trans-3-(2,2-dichlorovinyl)-2,2-dimethylcyclopropanecarboxylate was prepared. The yields obtained are indicated in Table VII.

The ratio of cis- to trans-ester obtained was 45:55.

TABLE VII

| Example No. | Water-soluble inorganic base | Amount (mmol) | Reaction time (hrs) | Ester Yield (%) |
|---|---|---|---|---|
| 34 | Anhydrous sodium carbonate | 12 | 8 | 98 |
| 35 | Sodium bicarbonate | 15 | 48 | 80 |
| 36 | Sodium hydroxide | 9 | 3 | 90 |
| 37 | Calcium carbonate | 15 | 48 | 85 |
| 38 | Lithium carbonate | 15 | 48 | 87 |

EXAMPLES 39 to 42

Preparation of 3-phenoxybenzyl cis, trans-3-(2,2-dichlorovinyl)-2,2-dimethylcyclopropanecarboxylate Following the procedure of Example 28, but using the phase-transfer catalyst as listed in Table VIII, 3-phenoxybenzyl cis, trans-3-(2,2-dichlorovinyl)-2,2-dimethylcyclopropanecarboxylate was prepared. The yields obtained are indicated in Table VIII.

The ratio of cis- to trans-ester obtained was 45:55.

TABLE VIII

| Example No. | Phase transfer catalyst | Amount (mmol) | Reaction time (hrs) | Ester Yield (%) |
|---|---|---|---|---|
| 39 | Tetrabutyl ammonium iodide | 0.3 | 3 | 92 |
| 40 | Benzyl triethyl ammonuim chloride | 0.3 | 5 | 94 |
| 41 | Tetrabutyl phosphonium bromide | 0.3 | 5 | 93 |
| 42 | 18-crown-6 | 0.15 | 5 | 95 |

We claim:

1. A process for the preparation of a pyrethroid ester compound of the general formula (I):

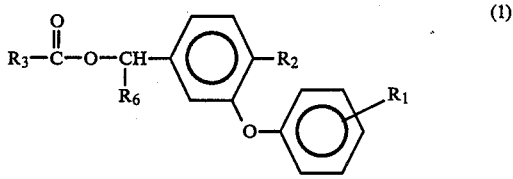

wherein $R_1$ and $R_2$ are the same or different from each other and represent a hydrogen or a halogen atom; $R_3$ represents

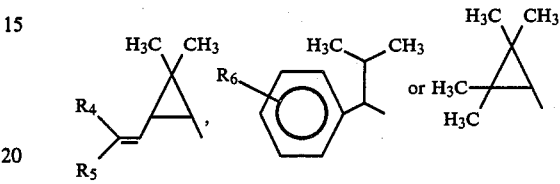

(wherein $R_4$ and $R_5$ represent a chlorine or bromine atom or a methyl group when $R_4$ is identical to $R_5$, but $R_4$ represents a chlorine or bromine atom or a methyl group and $R_3$ represents a trifluoromethyl group when $R_4$ is different from $R_5$, and $R_6$ represents a halogen atom or difluoromethoxy group); and $R_6$ represents a cyano group, which comprises reacting an organic acid of the general formula (II), an aldehyde of the general formula(III) and a water-soluble cyanide with a sulphonyl compound of the general formula(IV) wherein $R_7$ represents an aryl, alkyl or an optionally-substituted aryl and X is a halogen, azide, cyanide, imidazole, triazole, nitrotriazole or tetrazole, in the presence of a two-phase solvent system consisting of water and a substantially water-immiscible aprotic solvent and a phase transfer catalyst and then reacting the reaction mixture with a water-soluble inorganic base:

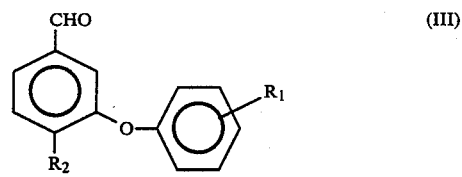

2. A process as claimed in claim 1, in which both $R_1$ and $R_2$ represent hydrogen and both $R_4$ and $R_5$ are chlorine atoms.

3. A process as claimed in claim 1, in which both $R_1$ and $R_2$ represent hydrogen, both $R_4$ and $R_5$ are chlorine atoms and the two hydrogen atoms in the cyclopropane ring moiety have a cis-configuration.

4. A process as claimed in claim 1, in which both $R_1$ and $R_2$ represent hydrogen, both $R_4$ and $R_5$ are bromine atoms, the two hydrogen atoms in the cyclopropane ring moiety have a cis-configuration and their carbon atoms have the R-designation configuration.

5. A process as claimed in claim 1, in which both $R_1$ and $R_2$ represent hydrogen, $R_4$ is a chlorine atom, $R_5$ is a trifluoromethyl group and the two hydrogen atoms in the cyclopropane ring moiety have a cis-configuration.

6. A process as claimed in claim 1, in which $R_1$ represents hydrogen, $R_2$ is a fluorine and both $R_4$ and $R_5$ represent chlorine atoms.

7. A process as claimed in claim 1, in which both $R_1$ and $R_2$ are hydrogen and para-located $R_6$ represents a chlorine atom.

8. A process as claimed in claim 1, in which both $R_1$ and $R_2$ are hydrogen, para-located $R_6$ represents a difluoromethoxy, and the α-carbon atom in the ketone has an S-configuration.

9. A process as claimed in claim 1, in which both $R_1$ and $R_2$ are hydrogen and $R_3$ represents a 2,2,3,3-tetramethyl cyclopropyl group.

10. A process as claimed in claim 1, in which para-located $R_1$ is a chlorine atom, $R_2$ is a fluorine, and both $R_4$ and $R_5$ represent chlorine atoms.

11. A process as claimed in claim 1, in which para-located $R_1$ is a chlorine atom, $R_2$ is a fluorine, $R_4$ is a chlorine, $R_5$ is a trifluoro-methyl group and the two hydrogen atoms in the cyclopropane ring moiety have a cis-configuration.

12. A process as claimed in claim 1, in which para-located $R_1$ is a chlorine, $R_2$ is a hydrogen, and both $R_4$ and $R_5$ represent chlorine atoms.

13. A process as claimed in claim 1, in which para-located $R_1$ is a chlorine, $R_2$ is a hydrogen, $R_4$ is a chlorine, $R_5$ is a trifluoromethyl group and the two hydrogen atoms in the cyclopropane ring moiety have a cis-configuration.

14. A process as claimed in claim 1, in which the sulphonyl compound of the general formula (IV) is p-toluene sulphonyl chloride, p-toluene sulphonyl bromide, methane sulphonyl chloride, benzene sulphonyl chloride, p-toluene sulphonyl cyanide or p-toluene sulphonyl azide.

15. A process as claimed in claim 1, in which the water-soluble inorganic base is anhydrous sodium carbonate, anhydrous potassium carbonate, sodium bicarbonate, sodium hydroxide, calcium carbonate, or lithium carbonate.

16. A process as claimed in claim 1, in which the phase transfer catalyst is selected from the group consisting of 1,4-diazabicyclo [2,2,2]octane, tetrabutyl ammonium bromide, 18-crown-6 and tetrabutyl phosphonium bromide.

17. A process for the preparation of a pyrethroid benzyl ester compound of the general formula(I):

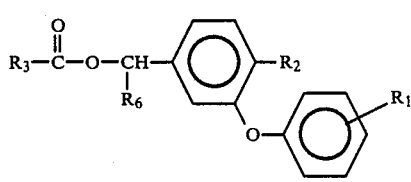

(I)

wherein $R_1$ and $R_2$ are the same or different from each other and represent a hydrogen or a halogen atom; $R_3$ represents

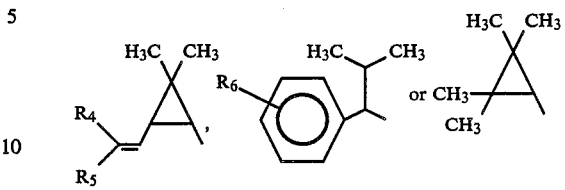

(wherein $R_4$ and $R_5$ represent a chlorine or bromine atom or a methyl group when $R_4$ is identical to $R_5$, but $R_4$ represents a chlorine or bromine atom or a methyl group and $R_5$ represents a trifluoromethyl group when $R_4$ is different from $R_5$, and $R_6$ represents a halogen atom or a difluoromethoxy group); and $R_8$ represents a hydrogen which comprises reacting an organic acid of the general formula(II), an alcohol of the general formula(III') and a water-soluble inorganic base with a sulphonyl compound of the general formula(IV) wherein $R_7$ represents an aryl, alkyl or an optionally-substituted aryl and X is a halogen, azide, cyanide, imidazole, triazole, nitrotriazole or tetrazole, in the presence of a two-phase solvent system consisting of water and a substantially water-immiscible aprotic solvent and a phase transfer catalyst:

(II)

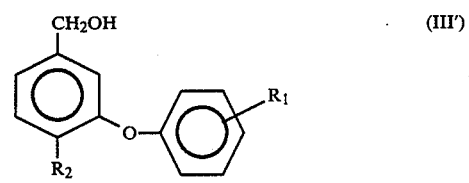

(III')

(IV)

18. A process as claimed in claim 17, in which the sulphonyl compound of the general formula (IV) is p-toluene sulphonyl chloride, p-toluene sulphonyl bromide, methane sulphonyl chloride, benzene sulphonyl chloride, p-toluene sulphonyl cyanide or p-toluene sulphonyl azide.

19. A process as claimed in claim 17, in which the water-soluble inorganic base is anhydrous sodium carbonate, anhydrous potassium carbonate, sodium bicarbonate, sodium hydroxide, calcium carbonate or lithium carbonate.

20. A process as claimed in claim 17, in which the phase transfer catalyst is selected from the group consisting of tetrabutyl ammonium iodide, benzyl triethyl ammonium chloride, tetrabutylphosphonium bromide, 18-crown-6 and 1,4-diazabicyclo [2,2,2] octane.

* * * * *